(12) United States Patent
Tanis et al.

(10) Patent No.: US 7,045,646 B2
(45) Date of Patent: May 16, 2006

(54) PROCESS TO PRODUCE ENANTIOMERICALLY ENRICHED ALCOHOLS AND AMINES

(75) Inventors: Steven P. Tanis, Carlsbad, CA (US); Bruce Evans, Kalamazoo, MI (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 155 days.

(21) Appl. No.: 10/804,295

(22) Filed: Mar. 19, 2004

(65) Prior Publication Data

US 2004/0230081 A1 Nov. 18, 2004

Related U.S. Application Data

(60) Provisional application No. 60/458,035, filed on Mar. 27, 2003, provisional application No. 60/457,791, filed on Mar. 26, 2003.

(51) Int. Cl.
*C07F 15/00* (2006.01)
*B01J 31/00* (2006.01)
*C07C 27/00* (2006.01)

(52) U.S. Cl. .................. 556/137; 502/155; 568/878
(58) Field of Classification Search ............... 556/137; 502/155; 568/878
See application file for complete search history.

(56) References Cited

FOREIGN PATENT DOCUMENTS

WO  WO 2004/014551  2/2004
WO  WO 2004/085058  10/2004

OTHER PUBLICATIONS

Noyori, R., et al., "Ruthenium(II)-Catalyzed Asymmetric Transfer Hydrogenation Of Ketones Using A Formic Acid-Triethylamine Mixture," 1996, J. Am. Chem. Soc., 2521-2522, vol. 118.
Noyori, R., et al., "The Catalyst Precursor, Catalyst, And Intermediate In The $Ru^{II}$ -Promoted Asymmetric Hydrogen Transfer Between Alcohols And Ketones," 1997, Angew: Chem. Int. Ed. Engl., 285-288, vol. 36, No. 3.
Fujii, et al., "Ruthenium(II)-Catalyzed Asymmetric Transfer Hydrogenation of Ketones Using a Formic Acid-Triethylamine Mixture," *Journal of American Chemical Society*, 1996, 2521-2522, vol. 118.
March, et al., "Aliphatic Nucleophilic Substitution," *Advanced Organic Chemistry: Reactions, Mechanisms, and Structure*, 1968, 251-375.
Noyori, et al., "Asymmetric Transfer Hydrogenation Catalyzed by Chiral Ruthenium Complexes," *Accounts of Chemical Research*, 1997, 97-102, vol. 30, No. 2.
Palmer, et al., "Asymmetric Transfer Hydrogenation of C=0 and C=N Bonds," *Tetrahedron: Asymmetry*, 1999, 2045-2061, vol. 10.
Vedejs, et al., "Substituted Isoquinolines by Noyori Transfer Hydrogenation: Enantioselective Synthesis of Chiral Diamines Contianing an Aniline Subunit," *Journal of Organic Chemistry*, 1999, 6724-6729, vol. 64.
Hashiguchi, S. et al., "Kinetic Resolution of racemic Secondary Alcohols by $Ru^{II}$ —Catalyzed Hydrogen Transfer," *Angew. Chem. Int. Ed. Engl.*, 1997, p. 288-290, vol. 36, No. 3.

*Primary Examiner*—Porfirio Nazario-Gonzalez
(74) *Attorney, Agent, or Firm*—Jeffrey H. Tidwell; Byran C. Zielinski

(57) ABSTRACT

This invention describes a convenient method for the preparation and use of a ruthenium catalyst for a chiral reduction of ketones and imines.

18 Claims, No Drawings

PROCESS TO PRODUCE ENANTIOMERICALLY ENRICHED ALCOHOLS AND AMINES

This application claims priority under 35 U.S.C. 119(e) to U.S. Application No. 60/458,035, filed Mar. 27, 2003, and 60/457,791, filed Mar. 26, 2003.

BACKGROUND OF THE INVENTION

Enantiomerically enriched (chiral) alcohols and amines are important compounds for use as pharmaceutical agents, intermediates for pharmaceutical agents, polymers, chelating agents, chiral auxiliaries and the like.

SUMMARY OF THE INVENTION

In general, the invention features a convenient method for the preparation and use of a ruthenium catalyst for a chiral reduction of ketones and imines.

In one aspect, the invention provides a method of producing a reducing catalyst by a) heating a mixture of a ligand, a ruthenium complex, a secondary alcohol and a tertiary amine; and b) removing the volatile components of the mixture. The mixture of step a may be heated to about 30° C. to about 150° C. The volatile components of the mixture may be removed under a reduced pressure of between about 0.05 to about 100 mm Hg. The secondary alcohol may be isopropanol.

In another aspect, the invention features a method for preparing a reducing catalyst by a) stirring a mixture of a ligand, a ruthenium complex, and a tertiary amine in a solvent followed by the addition of a 5:2 molar mixture of formic acid and triethyl amine. The solvent may include DMF.

In another aspect the invention provides a reducing catalyst produced by the process described above.

In another aspect, the invention features a method for reducing ketones and imines of Formula 1 to produce alcohols or amines of Formula 2;

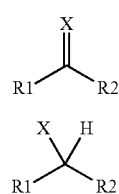

Formula 1

Formula 2 wherein in the compounds of formula 1,

R1 and R2 are independently selected from alkyl, alkenyl, cycloalkyl, heteroalkyl, cycloheteroalkyl, aryl, heteroaryl, substituted aryl and substituted heteroaryl; or R1 and R2 taken together may form a substituted or unsubstituted carbocyclic or heterocyclic ring of 3 to 12 members;

X is O or N—R3; and

R3 is alkyl, heteroalkyl, cycloalkyl, heteroalkyl, cycloheteroalkyl, aryl, heteroaryl, substituted aryl and substituted heteroaryl; and in the compounds of formula 2, $R^1$ and $R^2$ are as defined in Formula 1; X is —OH or —NHR3; and R3 is as defined for Formula 1.

The method includes a) stirring a mixture of a ligand, a ruthenium complex, and a tertiary amine in a solvent followed by the addition of a 5:2 molar mixture of formic acid and triethyl amine; and b) adding the ketone or imine to the mixture.

In another aspect, the method for reducing ketones and imines of Formula 1 includes a) heating a mixture of a ligand, a ruthenium complex, a secondary alcohol and a tertiary amine; b) removing the volatile components of the mixture; c) adding a solvent to the mixture; and d) adding the ketone or imine to the mixture.

Embodiments of these aspects of the invention may include one or more of the following features. The ligand is N-p-toluenesulfonyl-1,2-diphenylethylenediamine. The ruthenium complex is $RuCl_2(\square 6$-p-cymene). The tertiary amine is triethyl amine. The reducing catalyst is

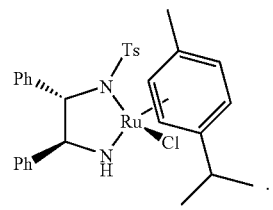

Advantageously, the present invention contemplates a reduction protocol that benefits from an unexpected solvent effect. In another aspect, this invention provides a simple preparation of the asymmetric reduction catalyst that requires nothing in the way of complex anaerobic, anhydrous manipulation, and produces a catalyst that is at once more reactive and more selective than catalyst prepared as described in the literature.

DETAILED DESCRIPTION OF THE INVENTION

Definitions

In the detailed description, the following definitions are used.

The term leaving group means a substituent which is subject to nucleophilic displacement to form a carbon—carbon or heteroatom-carbon bond as described in March, Advanced Organic Chemistry: Reactions, Mechanisms, and Structure, McGraw-Hill, pp. 251–375, 1968. Examples of leaving groups include, but are not limited to, chloro, bromo, iodo, arylsulfonyl and alkylsulfonyl.

The term "ee" means enantiomeric excess. For instance, one enantiomer of a specific compound is present in a mixture of the enantiomers for that compound at a greater amount relative to the other enantiomer. An enantiomerically enriched form may include a mixture of enantiomers of a specific compound in which the concentration of a single enantiomer of that compound is greater than 50%, more typically greater than 60%, 70%, 80%, or 90%, or higher (e.g., >95%, >97%, >99%, >99.5%), relative to the other enantiomer of that compound.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_8$ means 1–8 eight carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkene" by itself or as part of another substituent means a divalent radical derived from an alkane, as exemplified by —$CH_2CH_2CH_2CH_2$—. A "lower alkyl" or "lower alkene" is a shorter chain alkyl or alkene group, having eight or fewer carbon atoms.

The terms "alkoxy . . . alkylacylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Also included in the term "heteroalkyl" are those radicals described in more detail below as "heterocycloalkyl." The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "Fluoroalkyl," are meant to include monofluoroalkyl and polyfluoroalkyl.

The term "aryl," employed alone or in combination with other terms (e.g., aryloxy, arylthioxy, aralkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include, but are not limited to, phenyl, 1-naphthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-indolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl ring systems are selected from the group of acceptable substituents described below. The term "aralkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl . . . heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R"—SR', -halogen, —SiR'R"R, —OC(O)R', —C(O)R', —CO$_2$R', CONR'R", —OC(O)NR'R"—NR'C(O)R', —NR'—C(O)NR"R'", —NR"COOR", —NH—C(NH$_2$)=NH, —NR'C(NH$_2$)=N—H, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and X" each independently refer to hydrogen, unsubstituted C1—C0alkyl and heteroalkyl, unsubstituted aryl, aryl substituted with 1–3 halogens, unsubstituted alkyl, alkoxy or thioalkoxy groups, or aryl-(C1–C4)alkyl groups. When R' and R" are attached to the same nitrogen atom, they can be combined with the nitrogen atom to form a 3–7 membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: halogen, —OR, —OC(O)R, —NR'R", —SR, —R', —CN, —NO$_2$, —CO$_2$R', —CONR'R:', —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C1–C4)alkoxy, and perfluoro(C1–C4)alkyl, in a number ranging from zero to the total number of open valences on the aromatic ring system; and where R', R" and R'" are independently selected from hydrogen, (C1–C8)alkyl and heteroalkyl, unsubstituted aryl, (unsubstituted aryl)-(C1–C4)alkyl, and (unsubstituted aryloxy-($C_1$–$C_4$)alkyl.

Two of the substituents on adjacent atoms of the aryl ring may optionally be replaced with a substituent of the formula —S—C(O)—(CH$_2$)q-R—, wherein S and R are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_w$—B—, wherein A and B are independently —CH$_2$—, —O—, —NH—, —S—, —S(O)—, —S(O)$_2$—, —S(O)$_2$NR'— or a single bond, and w is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_w$-G-(CH$_2$)$_{w'}$—, where w and w' are independently integers of from 0 to 3, and G is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (Cl–C6)alkyl. As used herein, the term "heteroatom" is meant to include oxygen (O), nitrogen (N), and sulfur(S).

DESCRIPTION OF THE INVENTION

In one aspect, the present invention contemplates a general reduction protocol that benefits from a heretofore unappreciated solvent effect. In another aspect, this invention provides a simple preparation of the asymmetric reduction catalyst that requires nothing in the way of complex anaerobic, anhydrous manipulation, and produces a catalyst that is at once more reactive and more selective than catalyst prepared as described in the literature.

Methods for achieving the chiral reduction of ketones and imines include enantioselective hydride reduction, enantioselective hydrogenation and enantioselective transfer hydrogenation (see for example Palmer, M. J; et.al., Tetrahedron: Asymmetry, (1999), 10, 2045 and references cited therein).

In another aspect of this invention, the ketone A is reduced by enantioselective transfer hydrogenation using a modification of the method described by Noyori, et.al. (Noyori, R.; Hashiguchi, S., Accts. Chem. Res., (1997), 30, 97–102; Fujii, A.; Hashiguchi, S.; Uematsu, N.; Ikariya, T.; Noyori, R., J. Am. Chem. Soc. (1996), 118, 2521–2522). The modifications obviate the laborious chiral catalyst preparation and recrystallization as described by Noyori and others (Vedejs, E., et.al., J. Org. Chem. (1999), 64, 6724), and provides a simple, oxygen insensitive, catalyst preparation which enables the preparation of a variety of alcohols of Formula B. The catalyst can be prepared in advance and stored for a period of time without degradation in its performance. The present method also benefits from a heretofore unappreciated solvent effect. The use of a polar solvent such as dimethylformamide to give elevated yields in shorter time (48 hours reduced to 45 minutes) and with significantly improved enantioselection (ca. 60% ee improved to >99% ee). The use of solvents such as THF or methylene chloride did not prove advantageous. In preparing the catalyst, a mixture of a suitable ligand such as N-tosyl-1,2-diphenylethylenediamine and a suitable source of ruthenium complex such as RuCl$_2$(η6-p-cymene) dimer in a suitable secondary solvent alcohol such as isopropanol, 2-butanol, cyclohexanol and the like containing a suitable tertiary amine such as triethylamine is heated at 60–80° C. for 1 hour. Evaporation of the solvent gives the desired catalyst as a stable orange-brown solid (Method A). Alternatively, the catalyst can be prepared by combining the ligand, N-tosyl-1,2-diphenylethylenediamine and a ruthenium source such as RuCl$_2$(η6-p-cymene) dimer, in DMF, either DMF only or in the presence of a co-solvent such as methyl-tert-butyl ether (MTBE), followed by the addition of a 5:2 mixture (mole/mole) of formic acid and triethyl amine (Method B). If the reduction is being conducted by the preparation of the catalyst by Method A, the reduction is completed by the addition of polar solvent to the catalyst followed by a ketone of Formula A and a 5:2 to 1:1 (mole/mole) mixture of formic acid and triethylamine and stirring the mixture for 45 minutes to 6 hours, usually 45 minutes, at from –15° C. to room temperature, usually room temperature, at a pressure from 20 mmHg to 1 atm.

This invention then, describes a novel catalyst and process for the reduction of ketones and imines of Formula 1;

Formula I wherein R1 and R2 are independently selected from alkyl, alkenyl, cycloalkyl, heteroalkyl, cycloheteroalkyl, aryl, heteroaryl, substituted aryl and substituted heteroaryl;

X is O or N—R3; and

R3 is alkyl, heteroalkyl, cycloalkyl, heteroalkyl, cycloheteroalkyl, aryl, heteroaryl, substituted aryl and substituted heteroaryl; or R1 and R2 taken together may form a substituted or unsubstituted carbocyclic or heterocyclic ring of 3 to 12 members;

to give alcohols or amines of Formula 2

Formula 2 wherein R1 and R2 are as described for Formula 1; and

X is —OH or —NHR3, wherein R3 is as defined for Formula 1.

Examples of ketones and imines which may be reduced to the corresponding chiral alcohol or amine are shown in Table 1. The examples are illustrative only and not intended to limit the scope of reductions which may be carried out.

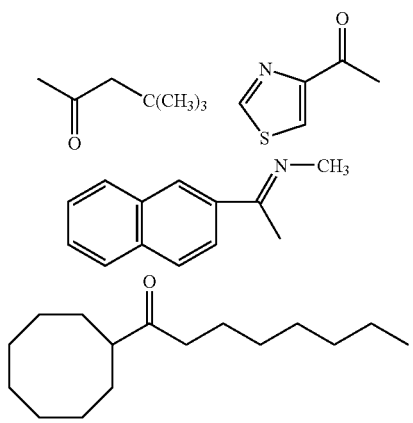

-continued

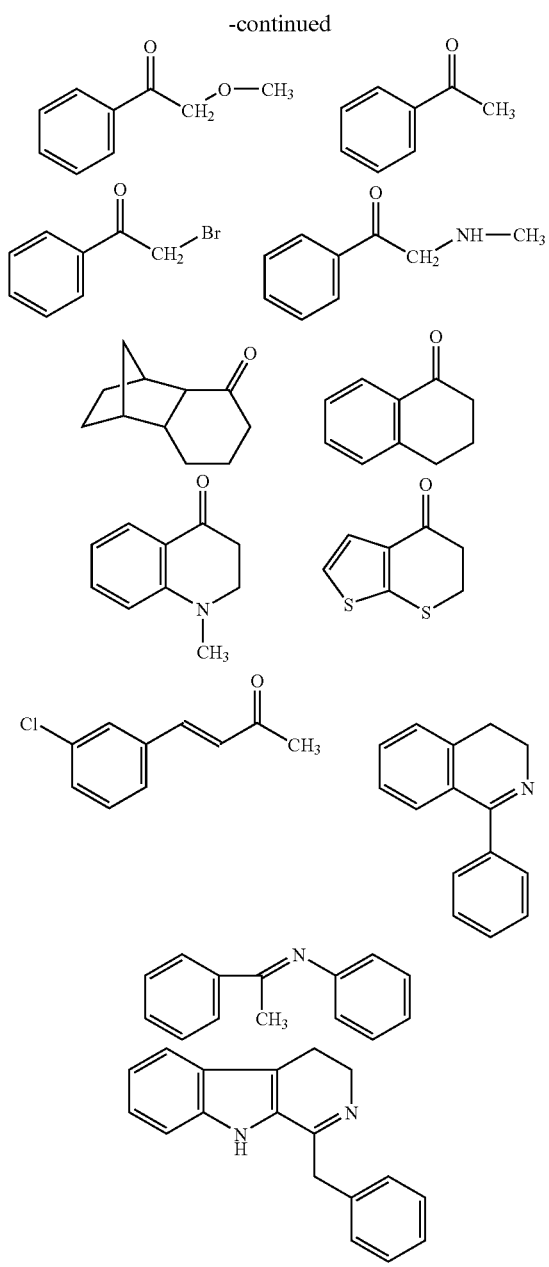

EXAMPLES

Example 1

Preparation of Catalyst—Method A

[RuCl$_2$(η$^6$-p-cymene)]$_2$ (0.84 g, 1.37 mmol), Et$_3$N (0.67 g, 6.66 mmol, 0.93 mL), and (1S, 2S)—N-p-toluenesulfonyl-1,2-diphenylethylenediamine (1.0 g, 2.72 mmol, 1.78 mol % based upon ketone) are combined in a 500 mL 1 N round bottom flask. Isopropanol (25 mL) and Et$_3$N (0.67 g, 6.66 mmol, 0.93 mL) are added, a reflux condenser is attached and the mixture is warmed under reflux for 1 hour. The mixture is cooled to room temperature and concentrated in vacuo to furnish the catalyst as a brown powdery solid.

Example 2

Reduction of 2-chloroacetyl pyridine

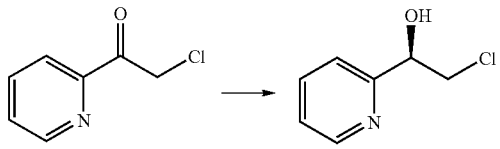

To the catalyst prepared in example 1 is added anhydrous DMF (Aldrich Sure Seal, 225 mL), followed in order by 2-chloroacetylpyridine (23.88 g, 0.153 mol) and HCOOH/Et$_3$N (5:2, Fluka, 55 mL). After ca. 2–3 minutes of stirring (room temperature) bubbles are apparent, emanating from the stirring vortex of the red-black solution. Reaction progress is monitored by reverse phase analytical HPLC, and after 75 minutes of stirring, the starting material had been consumed (95:5 NaH$_2$PO$_4$/H$_3$PO$_4$ buffered water/CH$_3$CN to 5:95, 17 minutes; retention time of starting chloroketone: 7.39 minutes, retention time of halohydrin 2.66 minutes). The reaction is quenched by adding MeOH (25 mL) and stirred 5 minutes. The solvents are removed in vacuo (cold finger rotovapor, vacuum pump) to give a red-black viscous oil. The crude material is taken up in Et$_2$O/CH$_2$Cl$_2$ (4:1, 1.25 L), placed in a 3 L separatory funnel, wash with saturated aq. NaHCO$_3$ (1.0 L), brine (1.0 L), and dried (Na$_2$SO$_4$). Filtration and concentration in vacuo afforded the crude product as a red-orange oil which is purified by chromatography on a column of silica gel (70 mm OD, 250 g 230–400 mesh, packed hexanes; compound applied in CH$_2$Cl$_2$/hexanes 60:40; eluted with hexanes/Et$_2$O (75:25 2 L; 65:35 2 L; 55:45 2 L; 350 mL fractions). Fractions 9–16 are combined to afford 14.72 g (61%) of the halohydrin as pale yellow solid. Physical Characteristics: MP: 47–48° C.; $^1$H-NMR (400 MHz, CDCl$_3$): δ=8.65, 7.92, 7.58, 7.44, 5.13, 4.60, 3.91; IR (neat): 3138, 3074, 3029, 3014, 2974, 2964, 2955, 2895, 2862, 2848, 2472, 2350, 2328, 2305, 2261 (w), cm$^{-1}$; Anal. Found: C, 53.23; H, 5.12; N, 8.82; Specific Rotation $[\alpha]^D_{25}$=−39 (c 0.94, CH$_2$Cl$_2$). (Chiral HPLC Analysis (Chiracel OJ): 98:2; 96% ee.

Example 3

Analysis of Optical Purity by Chiral Column Chromatography

Analysis of the optical purity of R-2-(1-hydroxy-2-chloroethyl)-pyridine: analysis is performed on a 0.46×25 CM Chiracel OJ column connected to a Gilson-Ranin HPLC system; with a solvent consisting of 2.5% i-PrOH in heptane, pumping at 0.5 mL/minute. The compound in question, as a solution in CH$_2$Cl$_2$ is injected (10 μL) at time=0 and the UV detector is set at 220 nm. At time=45.23 minutes a peak with an integrated area of 98 area % is detected; at time=47.77 a peak with an integrated area of 2 area % is detected, representative of a 98:2 ratio, 96% ee.

Example 4

Demonstration of Solvent Effect

Table 2 summarizes the results of reducing 3-chloroacetylpyridine. The reductions are conducted according to the procedure of Example 1 with the exception that solvent and pressure are varied as listed in the Table.

TABLE 2

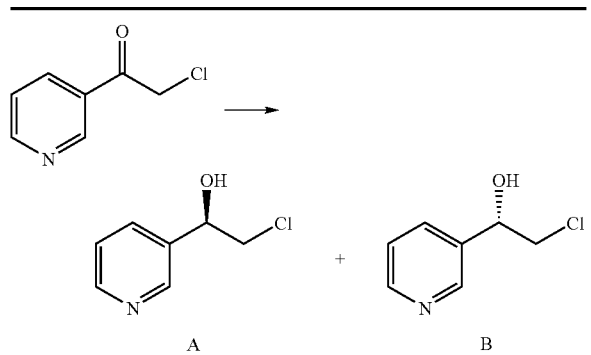

| Et$_3$N/HCOOH + Solvent | Time | Overall Yield(%) | Ratio of A/B | Pressure (mm Hg) |
|---|---|---|---|---|
| None | 48 h | 27 | 80/20 | atm |
| CH$_2$Cl$_2$ | 16 h | 39 | 85:15 | atm |
| THF | 16 h | 37 | 83:17 | atm |
| DMF | 16 h | 67 | 95/5 | atm |
| DMF | 0.75 h | 80 | 100/0 | 40 |

Example 4

Reduction of 2-chloroacetylfuran to S-1-(2-furyl)-2-chloroethanol

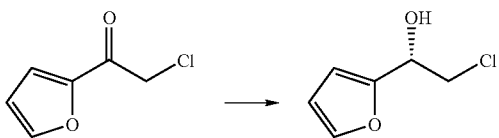

[RuCl$_2$(η$^6$-p-cymene)]$_2$ (0.99 g, 1.61 mmol), Et$_3$N (0.67 g, 6.66 mmol, 0.93 mL), and (1R, 2R)—N-p-toluenesulfonyl-1,2-diphenylethylenediamine (1.18 g, 3.22 mmol, 2.25 mol % based upon ketone) are combined in a 500 mL 1 N round bottom flask. i-PrOH (25 mL) and Et$_3$N (0.67 g, 6.66 mmol, 0.93 mL) are added, a reflux condenser is attached and the mixture is warmed under reflux, and maintained, for 1 hour. Cool to room temperature and concentrate in vacuo (rotovapor) to furnish the catalyst as an orange-brown powdery solid. To the catalyst is added anhydrous DMF (Aldrich Sure Seal, 250 mL), followed in order by 2-chloroacetylfuran (20.6 g, 0.143 mol) and HCOOH/Et$_3$N (5:2, Fluka, 51 mL). After ca. 2–3 minutes of stirring (room temperature) bubbles (presumed to be CO$_2$) are apparent, emanating from the stirring vortex of the red-black solution. Reaction progress is monitored by reverse phase analytical HPLC, and after 65 minutes of stirring, the starting material had been consumed (95:5 NaH$_2$PO$_4$/H$_3$PO$_4$ buffered water/CH$_3$CN to 5:95, 17 minutes; retention time of starting chloroketone: 6.70 minutes, retention time of halohydrin 6.35 minutes). Quench the reaction by adding MeOH (25 mL), stir 5 minutes and then the reaction mixture is poured into ice-water (1 L) and the aqueous phase is saturated with salt. The mixture is transferred to a 2 L separatory funnel with ether (500 mL), shaken, and the organic phase is removed. The aqueous layer is extracted with ether (3×250 mL) and the combined organic layers are washed with saturated aq. NaHCO$_3$ (0.5 L), brine (4×250 mL), and dried (Na$_2$SO$_4$). Filtration and concentration in vacuo afforded the crude product as a red-orange oil (20.5 g) that is triturated with ether/pentane (10:90, 4×100 mL). The combined triturates are concentrated in vacuo (take care as the halohydrin is volatile, hence the choice of ether/pentane as triturant and no removal of DMF in vacuo) to furnish the desired halohydrin (15.97 g, 76%) in good purity as determined by HPLC and $^1$H-NMR. Physical Characteristics: $^1$H-NMR (400 MHz, CDCl$_3$): δ=7.41, 6.37, 4.95, 3.85, 2.58; IR (diffuse reflectance) 1428, 1422, 1221, 1205, 1198, 1166, 1096, 1021, 953, 924, 883, 789, 738, 714, 666, cm$^{-1}$; MS (EI) m/z (rel. intensity) 146 (17), 129 (2), 98 (6), 97 (base), 95 (3), 94 (1), 69 (3), 41 (2); HRMS (EI) found 146.0136; Specific Rotation [α]$^D_{25}$=17 (c 0.97, methanol); Chiral HPLC Analysis (Chiracel OJ): 99:1; 98% ee.

Example 5

Reduction of 2-chloroacetyl pyridine (Catalyst Preparation Method B)

(1R, 2R)—N-p-toluenesulfonyl-1,2-diphenylethylenediamine (1.103 g, 3.01 mmol), [RuCl$_2$(η$^6$-p-cymene)]$_2$ (0.936 g, 1.528 mmol), and triethylamine (0.072 g, 0.71 mmol) in 5 ml DMF are combined in a 50 ml 3-neck round bottom flask. The mixture is allowed to stir for 1 hr at room temperature, then a solution of 2-chloroacetyl pyridine (3.7 g, 19.7 mmol) in MTBE (15 mL) is added in one portion and the flask is rinsed with DMF (10 mL) which is added to the reaction vessel. A gentle flow of nitrogen (~5 ml/second) is then initiated and bubbled through the reaction mixture. To this solution is added 8.06 mL of a 5:2 (mole/mole) mixture of formic acid/triethyl amine in one portion. An endotherm is observed over the next 30 min with the temp dropping from 22° C. to 12° C. The mixture is stirred for 1 hr @ RT. HPLC (3drops reaction diluted in 1 ml methanol) showed no detectable 2-chloroacetyl pyridine (RT=5.4 min) and 97.5 area % S-2-(1-hydroxy-2-chloroethyl)-pyridine (RT=3.40 min) (Agilent HPLC 50:50 acetonitrile: 0.1M NH$_4$OAc, 1 ml/min, detection at 254 nm, 250×4.6 mm Zorbax RX-C8).

What is claimed is:

1. A method of producing a reducing catalyst, comprising:
   a) heating a mixture of a ligand, a ruthenium complex, a secondary alcohol and a tertiary amine; and
   b) removing the volatile components of the mixture, wherein said method is performed in the presence of oxygen.

2. The method of claim 1, wherein the mixture of step a is heated from about 30° C. to about 150° C.

3. The method of claim 1, wherein the volatile components of the mixture are removed under a reduced pressure of between about 0.05 mm Hg to about 100 mm Hg.

4. The method of claim 1, wherein the secondary alcohol is isopropanol.

5. A method for preparing a reducing catalyst, comprising:
   a) stirring a mixture of a ligand, a ruthenium complex, and a tertiary amine in a solvent; and
   b) adding a 5:2 molar mixture of formic acid and triethyl amine.

6. The method of claim 5, wherein the solvent comprises DMF.

7. The method of claim 1, wherein the ligand is N-p-toluenesulfonyl-1 2-diphenylethylenediamine.

8. The method of claim 1, wherein the ruthenium complex is RuCl$_2$(η6-p-cymene).

9. The method of claim 1, wherein the tertiary amine is triethyl amine.

10. The method of claim 1, wherein the reducing catalyst is

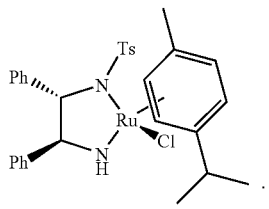

11. A method for reducing ketones and imines of Formula 1;

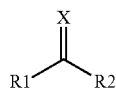

Formula I wherein R1 and R2 are independently selected from alkyl, alkenyl, cycloalkyl, heteroalkyl, cycloheteroalkyl, aryl, heteroaryl, substituted aryl and substituted heteroaryl;
  X is O or N-R3; and
  R3 is alkyl, heteroalkyl, cycloalkyl, heteroalkyl, cycloheteroalkyl, aryl, heteroaryl, substituted aryl and substituted heteroaryl; or
  R1 and R2 taken together may form a substituted or unsubstituted carbocyclic or heterocyclic ring of 3 to 12 members;
to produce alcohols or amines of Formula 2

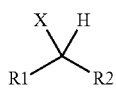

Formula 2 wherein R1 and R2 are as described for Formula 1; and
  X is —OH or —NHR3, wherein R3 is as defined for Formula 1;
said method comprising:
  a) stirring a mixture of a ligand, a ruthenium complex, and a tertiary amine in a solvent followed by the addition of a 5:2 molar mixture of formic acid and triethyl amine; and
  b) adding the ketone or imine to the mixture.

12. The method of claim 11, wherein the solvent comprises DMF.

13. The method of claim 11, wherein the ligand is N-p-toluenesulfonyl-1,2-diphenylethylenediamine.

14. The method of claim 11, wherein the ruthenium complex is $RuCl_2(\eta 6\text{-p-cymene})$.

15. A method for reducing ketones and imines of Formula 1;

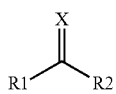

Formula I wherein R1 and R2 are independently selected from alkyl, alkenyl, cycloalkyl, heteroalkyl, cycloheteroalkyl, aryl, heteroaryl, substituted aryl and substituted heteroaryl;
  X is 0 or N—R3; and
  R3 is alkyl, heteroalkyl, cycloalkyl, heteroalkyl, cycloheteroalkyl, aryl, heteroaryl, substituted aryl and substituted heteroaryl; or
  R1 and R2 taken together may form a substituted or unsubstituted carbocyclic or heterocyclic ring of 3 to 12 members;
to produce alcohols or amines of Formula 2

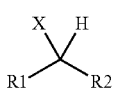

Formula 2 wherein R1 and R2 are as described for Formula 1; and
  X is —OH or —NHR3, wherein R3 is as defined for Formula 1;
said method comprising:
  a) heating a mixture of a ligand, a ruthenium complex, a secondary alcohol and a tertiary amine;
  b) removing the volatile components of the mixture;
  c) adding a solvent to the mixture; and
  d) adding the ketone or imine to the mixture, wherein said method is performed in the presence of oxygen.

16. The method of claim 15, wherein the solvent comprises DMF.

17. The method of claim 15, wherein the ligand is N-p-toluenesulfonyl-1,2-diphenylethylenediamine.

18. The method of claim 15, wherein the ruthenium complex is $RuCl_2(\eta 16\text{-p-cymene})$.

* * * * *